(12) United States Patent
Hahn et al.

(10) Patent No.: US 8,344,081 B2
(45) Date of Patent: Jan. 1, 2013

(54) TRANSITION METAL COMPLEXES, CATALYSTS COMPOSITION CONTAINING THE SAME, AND PROCESS FOR PREPARING ETHYLENE HOMOPOLYMERS OR COPOLYMERS OF ETHYLENE AND ALPHA-OLEFINS USING THE SAME

(75) Inventors: Jong-Sok Hahn, Daejeon (KR); Myung-Ahn Ok, Daejeon (KR); Dong-Cheol Shin, Daejeon (KR); Ho-Seong Lee, Seoul (KR); Sang-Ook Kang, Yongin-si (KR); Tae-Jin Kim, Seoul (KR)

(73) Assignee: SK Innovation Co., Ltd. (KR)

( * ) Notice: Subject to any disclaimer, the term of this patent is extended or adjusted under 35 U.S.C. 154(b) by 101 days.

(21) Appl. No.: 12/808,257

(22) PCT Filed: Oct. 30, 2008

(86) PCT No.: PCT/KR2008/006411
§ 371 (c)(1),
(2), (4) Date: Jun. 15, 2010

(87) PCT Pub. No.: WO2009/084805
PCT Pub. Date: Jul. 9, 2009

(65) Prior Publication Data
US 2010/0298512 A1  Nov. 25, 2010

(30) Foreign Application Priority Data
Dec. 31, 2007  (KR) .................. 10-2007-0141887

(51) Int. Cl.
C08F 4/643  (2006.01)
C08F 4/6592  (2006.01)
B01J 31/22  (2006.01)
C07F 17/00  (2006.01)

(52) U.S. Cl. ........ 526/160; 526/133; 526/134; 526/165; 526/348; 526/352; 526/943; 502/103; 502/152; 556/53

(58) Field of Classification Search .................. 556/53; 526/134, 160, 165, 348, 352, 943, 133; 502/103, 502/152
See application file for complete search history.

(56) References Cited

U.S. PATENT DOCUMENTS

| | | | |
|---|---|---|---|
| 2,952,697 A * | 9/1960 | Gorsich ................. 556/43 |
| 4,752,597 A | 6/1988 | Turner | |
| 5,079,205 A | 1/1992 | Canich | |
| 5,461,127 A * | 10/1995 | Naganuma et al. ......... 526/127 |
| 6,300,447 B1 | 10/2001 | Johoji et al. | |
| 6,323,149 B1 | 11/2001 | Takemori et al. | |
| 6,329,478 B1 | 12/2001 | Katayama et al. | |
| 2007/0004586 A1 * | 1/2007 | Woo et al. ................. 502/117 |
| 2007/0135297 A1 | 6/2007 | Woo et al. | |
| 2007/0249490 A1 | 10/2007 | Ok et al. | |

FOREIGN PATENT DOCUMENTS

| | | |
|---|---|---|
| CN | 101077879 | 11/2007 |
| EP | 0320762 | 6/1989 |
| EP | 0372632 | 6/1990 |
| EP | 0416815 | 3/1991 |
| EP | 0420436 | 4/1991 |
| EP | 0842939 | 5/1998 |
| JP | 63-092621 | 4/1988 |
| JP | 02-084405 | 3/1990 |
| JP | 03-002347 | 1/1991 |
| KR | 10-2001-0074722 | 8/2001 |
| KR | 10-0639696 | 10/2006 |
| KR | 10-1060838 | 8/2011 |

OTHER PUBLICATIONS

Kotohiro Nomura et al., •Synthesis of Various Nonbridged Titanium (Iv) Cyclopentadienyl-Aryloxy Complexes of the Type CpTi(OAr)X2 and Their Use in the Catalysis of Alkene Polymerization. Important Roles of Substituents on Both Aryloxy and Cyclopentadienyl Groups, Organometallics, 1998, pp. 2152-2154 vol. 17, American Chemical Society, Japan.
International Search Report—PCT/KR2008/006411 dated Jun. 9, 2009.
Korean Office Action—Korean Application No. 10-2007-0141887 issued on Oct. 10, 2011, citing KR 10-0639696 and KR 10-2007-0104845.
A. J. Nielson, et al., Steric influences in cyclopentadienyl-monophenoxide complexes of titanium(iv) arising from ortho-substitution of the phenoxide ligand, Polyhedron 25, 2006, p. 1729-1736.
W. Skupinski, et al., Synthesis and Properties, Journal of Organometallic Chemistry, 220, 1981, p. 39-44.

* cited by examiner

*Primary Examiner* — Caixia Lu
(74) *Attorney, Agent, or Firm* — Cantor Colburn LLP

(57) ABSTRACT

The present invention relates to a transition metal complex useful as a transition metal catalyst in the preparation of an ethylene homopolymer or a copolymer of ethylene and an α-olefin, a catalyst composition comprising the same and a process of preparing an ethylene homopolymer or a copolymer of ethylene and an α-olefin using the same. More particularly, it relates to a transition metal complex having a cyclopentadiene derivative and at least one phenyl oxide ligand substituted at the 2-position of phenyl with, for example, a silyl group having a $C_1$-$C_{30}$ hydrocarbon group or a $C_1$-$C_{20}$ hydrocarbon group, around a group IV transition metal, with no crosslinkage between the ligands, a catalyst composition comprising the transition metal complex and a cocatalyst selected from the group consisting of an aluminoxane and a boron compound, and a process for preparing an ethylene homopolymer or a copolymer of ethylene and an α-olefin using the same.

7 Claims, 1 Drawing Sheet

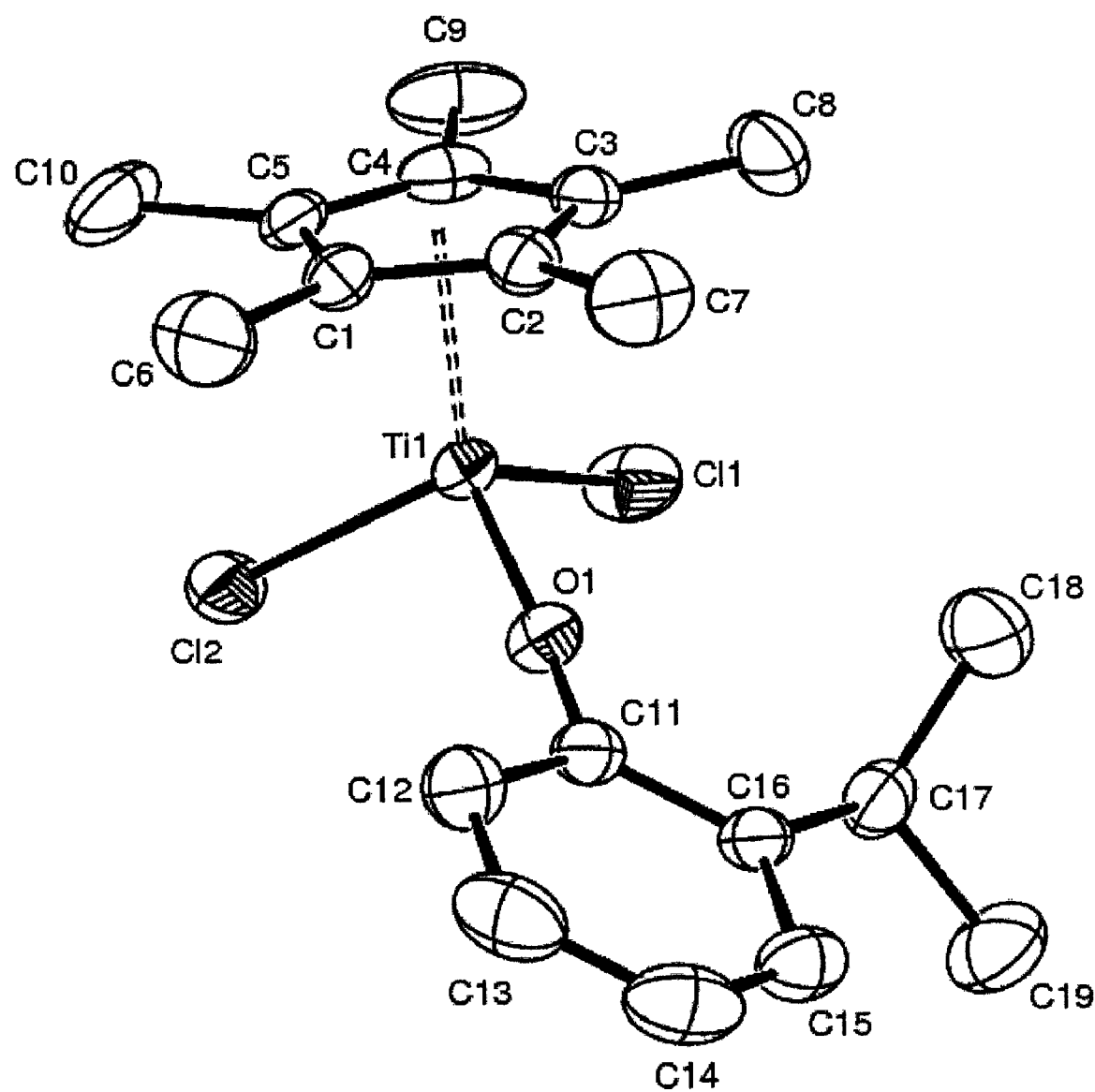

TRANSITION METAL COMPLEXES, CATALYSTS COMPOSITION CONTAINING THE SAME, AND PROCESS FOR PREPARING ETHYLENE HOMOPOLYMERS OR COPOLYMERS OF ETHYLENE AND ALPHA-OLEFINS USING THE SAME

TECHNICAL FIELD

The present invention relates to a transition metal complex useful as a transition metal catalyst in the preparation of an ethylene homopolymer or a copolymer of ethylene and an α-olefin, a catalyst composition comprising the same and a process of preparing an ethylene homopolymer or a copolymer of ethylene and an α-olefin using the same. More particularly, it relates to a transition metal complex having a cyclopentadiene derivative and at least one phenyl oxide ligand substituted at the 2-position of phenyl with, for example, a silyl group having a $C_1$-$C_{30}$ hydrocarbon group or a $C_1$-$C_{20}$ hydrocarbon group, around a group IV transition metal, with no crosslinkage between the ligands, a catalyst composition comprising the transition metal complex and a cocatalyst selected from the group consisting of an aluminoxane and a boron compound, and a process for preparing an ethylene homopolymer or a copolymer of ethylene and an α-olefin using the same.

BACKGROUND ART

Conventionally, Ziegler-Natta catalyst systems comprising titanium or vanadium compounds as main catalyst and alkylaluminum compounds as cocatalyst have been used to prepare ethylene homopolymers or copolymers of ethylene and α-olefins. Although the Ziegler-Natta catalyst system provides good efficiency of ethylene polymerization, the resulting polymers tend to have a broad molecular weight distribution because of the heterogeneousness of catalytic active sites. In particular, the resulting copolymer of ethylene and an α-olefin has no uniform compositional distribution.

Recently, the so-called metallocene catalyst system, which comprises metallocene compounds of group IV transition metals, e.g. titanium, zirconium or hafnium, and methylaluminoxane as cocatalyst, has been developed. Because this catalyst system is a homogeneous cocatalyst having homogeneous catalytic active sites, it is capable of preparing polyethylenes having a narrower molecular weight distribution and a more uniform compositional distribution as compared to the Ziegler-Natta catalyst system. For example, European Patent Publication Nos. 320,762 and 372,632 or Japanese Patent Laid-Open Nos. Sho 63-092621, Hei 02-84405 and Hei 03-2347 disclose that polyethylenes having a molecular weight distribution ($M_w/M_n$) of 1.5-2.0 can be prepared efficiently from ethylene by activating the metallocene compounds $Cp_2TiCl_2$, $Cp_2ZrCl_2$, $Cp_2ZrMeCl$, $Cp_2ZrMe_2$, ethylene $(IndH_4)_2ZrCl_2$, etc. with the cocatalyst methylaluminoxane. However, it is difficult to obtain high molecular weight polymers with this catalyst system. Especially, when applied to solution polymerization performed at high temperature, i.e. 140° C. or higher, it is not suitable to prepare high molecular weight polymers having a weight average molecular weight ($M_w$) of 100,000 or higher because the polymerization efficiency decreases rapidly and the elimination of β-hydrogen prevails.

Recently, the so-called geometrically constrained non-metallocene catalyst system (also known as the single-site catalyst) enables the preparation of high molecular weight polymers through homopolymerization of ethylene or copolymerization of ethylene and an α-olefin under the solution polymerization condition, in which a transition metal is connected as a ring. European Patent Publication Nos. 0416815 and 0420436 disclose a compound in which an amide group is connected to a cyclopentadiene ligand to form a ring.

And, European Patent Publication No. 0842939 discloses an electron donor compound catalyst in which a phenol-based ligand and a cyclopentadiene ligand are connected to form a ring. However, the geometrically constrained catalyst is inappropriate for commercial application because the yield of the ring forming reaction between the ligand and the transition metal compound in the synthesis of the catalyst is very low.

U.S. Pat. No. 6,329,478 and Korean Patent Publication No. 2001-0074722 disclose non-geometrically constrained, non-metallocene catalysts that can be used under hot solution condition. These patents disclose that single-site catalysts having at least one phosphinimine compound as ligand provide superior ethylene transition ratio during the copolymerization of ethylene and an α-olefin by solution polymerization under high temperature condition of 140° C. or higher. However, specific phosphine compounds have to be used to synthesize the phosphinimine ligand. These compounds are inappropriate for large-scale olefin polymer production because they are harmful to the environment and humans. U.S. Pat. No. 5,079,205 discloses a catalyst having a bisphenyl oxide ligand, but it has too low a catalytic activity to be commercially applicable.

In addition, synthesis of a phenyl oxide ligand in which the phenyls of 2- and 6-positions are substituted by alkyl groups as non-metallocene catalyst and polymerization using the same are reported by Nomura et al. [Organometallics 1998, 17, 2152]. But, its application is restricted to the preparation of higher-grade copolymers of α-olefins in good yield, because of the steric hindrance by the substituents of the phenyl oxide ligand.

The above information disclosed in this Background section is only for enhancement of understanding of the background of the invention and therefore it may contain information that does not form the related art that is already known in this country to a person of ordinary skill in the art.

DISCLOSURE

Technical Problem

The inventors of the present invention have carried out extensive researches to solve the aforesaid problems associated with the related art. As a result, they have found that a non-crosslinked transition metal catalyst having a cyclopentadiene derivative and at least one phenyl oxide ligand substituted at the 2-position of phenyl with a silyl group having a $C_1$-$C_{30}$ hydrocarbon group or a $C_1$-$C_{20}$ hydrocarbon group exhibits superior catalytic activity for the polymerization of olefin. Based on this finding, they have developed a catalyst which can be applied in an olefin polymerization process performed at 80° C. or higher to provide high molecular weight olefin homopolymers or copolymers with good efficiency.

Accordingly, an object of the present invention is to provide a transition metal compound having a non-crosslinked structure, being synthesized very economically, providing excellent catalytic activity for the polymerization of olefin and enabling very efficient copolymerization of α-olefins, a catalyst composition comprising the same, and a process for commercial and economical polymerization copolymers of ethylene and α-olefins with various physical properties using the transition metal and the transition metal catalyst composition.

Technical Solution

To attain the object, in an aspect, the present invention provides a transition metal complex represented by the following Chemical Formula 1, more specifically, one having a cyclopentadiene derivative and at least one phenyl oxide ligand substituted at the 2-position of phenyl with, for example, a silyl group having a $C_1$-$C_{30}$ hydrocarbon group or a $C_1$-$C_{20}$ hydrocarbon group, around a group IV transition metal as center metal, with no crosslinkage between the ligands:

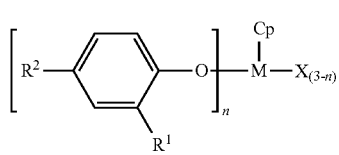

[Formula 1]

where M is a group IV transition metal; Cp is capable of forming a $\eta^5$-bonding with M, and is a cyclopentadienyl ring unsubstituted or substituted by $C_1$-$C_{20}$ alkyl, $C_6$-$C_{30}$ aryl, $C_2$-$C_{20}$ alkenyl or $C_6$-$C_{30}$ aryl $C_1$-$C_{20}$ alkyl, or a fused ring unsubstituted or substituted by $C_1$-$C_{20}$ alkyl, $C_6$-$C_{30}$ aryl, $C_2$-$C_{20}$ alkenyl or $C_6$-$C_{30}$ aryl $C_1$-$C_{20}$ alkyl having a cyclopentadienyl ring; $R^1$ is $C_1$-$C_{20}$ alkyl, $C_3$-$C_{20}$ cycloalkyl, $C_6$-$C_{30}$ aryl, $C_1$-$C_{20}$ alkyl $C_6$-$C_{30}$ aryl, $C_1$-$C_{20}$ alkyl-substituted or $C_6$-$C_{30}$ aryl-substituted silyl, $C_6$-$C_{30}$ aryl $C_1$-$C_{10}$ alkyl, $C_1$-$C_{20}$ alkoxy, $C_1$-$C_{20}$ aryl-substituted siloxy, $C_1$-$C_{20}$ alkyl-substituted or $C_6$-$C_{30}$ aryl-substituted amino, $C_1$-$C_{20}$ alkyl-substituted or $C_6$-$C_{30}$ aryl-substituted phosphido, $C_1$-$C_{20}$ alkyl-substituted mercapto, or nitro; $R^2$ is hydrogen, halogen, linear or branched $C_1$-$C_{20}$ alkyl optionally substituted by one or more halogen, linear or branched $C_1$-$C_{20}$ alkyl-substituted silyl optionally substituted by one or more halogen, $C_6$-$C_{30}$ aryl optionally substituted by one or more halogen, $C_6$-$C_{30}$ aryl $C_1$-$C_{10}$ alkyl optionally substituted by one or more halogen, $C_1$-$C_{20}$ alkoxy optionally substituted by one or more halogen, $C_3$-$C_{20}$ aryl-substituted siloxy, $C_1$-$C_{20}$ alkyl-substituted or $C_6$-$C_{30}$ aryl-substituted amino, $C_1$-$C_{20}$ alkyl-substituted or $C_6$-$C_{30}$ aryl-substituted phosphine, $C_1$-$C_{20}$ alkyl-substituted mercapto, or nitro; n is an integer 1 or 2; and X is independently halogen, $C_1$-$C_{20}$ alkyl, $C_3$-$C_{20}$ cycloalkyl, $C_6$-$C_{30}$ aryl $C_1$-$C_{20}$ alkyl, $C_1$-$C_{20}$ alkoxy, $C_3$-$C_{20}$ alkylsiloxy, $C_1$-$C_{20}$ alkyl-substituted or $C_6$-$C_{30}$ aryl-substituted amino, $C_1$-$C_{20}$ alkyl-substituted or $C_6$-$C_{30}$ aryl-substituted phosphine, or $C_1$-$C_{20}$ alkyl-substituted mercapto.

In another aspect, the present invention provides a transition metal catalyst composition for the preparation of an ethylene homopolymer or a copolymer of ethylene and an α-olefin comprising: the above transition metal complex and; an alkylaluminoxane or organoaluminum cocatalyst, or a boron compound cocatalyst. In another aspect, the present invention provides a process for preparing an ethylene homopolymer or a copolymer of ethylene and an α-olefin using the transition metal complex or the catalyst composition, and an ethylene homopolymer or a copolymer of ethylene and an α-olefin prepared using the same.

Hereinafter, reference will now be made in detail to various embodiments of the present invention, examples of which are illustrated in the accompanying drawing and described below. While the invention will be described in conjunction with example embodiments, it will be understood that the present description is not intended to limit the invention to those example embodiments. On the contrary, the invention is intended to cover not only the example embodiments, but also various alternatives, modification, equivalents and other embodiments, which may be included within the spirit and scope of the invention as defined in the appended claims.

In the transition metal catalyst represented by Chemical Formula 1, M is preferably titanium, zirconium or hafnium. And, Cp is a derivative having a fused ring unsubstituted or substituted by $C_1$-$C_{20}$ alkyl, $C_6$-$C_{30}$ aryl, $C_2$-$C_{20}$ alkenyl or $C_6$-$C_{30}$ aryl $C_1$-$C_{20}$ alkyl having a cyclopentadiene anion or a cyclopentadienyl ring capable of forming a $\eta^5$-bonding with the center metal as a backbone. Specific examples may include cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, florenyl, methylflorenyl, dimethylflorenyl, ethylfiorenyl, isopropylflorenyl, etc.

The substituent $R^1$ substituted at the 2-position of the phenyl oxide ligand may be: linear or branched $C_1$-$C_{20}$ alkyl, e.g. methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl or n-eicosyl, preferably methyl, ethyl, isopropyl or tert-butyl; $C_3$-$C_{20}$ cycloalkyl, e.g. cyclopropane, cyclobutyl, cyclopentyl, cyclohexyl, cycloheptyl or adamantyl, preferably cyclopentyl or cyclohexyl; $C_6$-$C_{30}$ aryl or $C_1$-$C_{20}$ alkyl $C_6$-$C_{30}$ aryl, e.g. phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, florenyl, triphenyl, naphthyl or anthracenyl, preferably phenyl, naphthyl, biphenyl(biphenyl), 2-isopropylphenyl, 3,5-xylyl or 2,4,6-trimethylphenyl; $C_6$-$C_{30}$ aryl $C_1$-$C_{10}$ alkyl, e.g. benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-decylphenyl)methyl, (n-tetradecylphenyl)methyl, triphenylmethyl, naphthylmethyl or anthracenylmethyl, preferably benzyl or triphenylmethyl; $C_1$-$C_{20}$ alkyl-substituted or $C_6$-$C_{30}$ aryl-substituted silyl, e.g. methylsilyl, ethylsilyl, phenylsilyl, dimethylsilyl, diethylsilyl, diphenylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyldimethylsilyl, tri-n-pentylsilyl, tri-n-hexylsilyl, or triphenylsilyl, preferably trimethylsilyl, tert-butyldimethylsilyl or triphenylsilyl; $C_1$-$C_{20}$ alkoxy, e.g. methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy or n-eicosoxy, preferably methoxy, ethoxy, isopropoxy or tert-butoxy; or $C_3$-$C_{20}$ alkylsiloxy, e.g. trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyldimethylsiloxy, tri-n-pentylsiloxy, tri-n-hexylsiloxy or tricyclohexylsiloxy, preferably trimethylsiloxy or tert-butyldimethylsiloxy; $C_1$-$C_{20}$ alkyl-substituted or $C_6$-$C_{30}$ aryl-substituted amino, e.g. dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bistrimethylsilylamino or bis-tert-butyldimethylsilylamino, or corresponding alkyl-substituted phosphine, preferably dimethylamino, diethylamino or diphenylamino; $C_1$-$C_{20}$ alkyl-substituted or $C_6$-$C_{30}$ aryl-substituted phosphine, e.g. dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, dibenzylphosphine, methylethylphosphine, methylphenylphosphine, benzylhexylphosphine, bistrimethylsilylphosphine or bis-tert-butyldimethylsilylphosphine, preferably dimethylphosphine, diethylphosphine or diphenylphosphine.

The substituent $R^2$ substituted at the 4-position of the phenyl oxide ligand may be: linear or branched $C_1$-$C_{20}$ alkyl, e.g. methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl or n-eicosyl, preferably methyl, ethyl, isopropyl or tert-butyl; $C_6$-$C_{30}$ aryl or $C_1$-$C_{20}$ alkyl $C_6$-$C_{30}$ aryl, e.g. phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl(biphenyl), florenyl, triphenyl, naphthyl or anthracenyl, preferably phenyl, naphthyl, biphenyl(biphenyl), 2-isopropylphenyl, 3,5-xylyl or 2,4,6-trimethylphenyl; $C_6$-$C_{30}$ aryl $C_1$-$C_{10}$ alkyl, e.g. benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-decylphenyl)methyl, (n-tetradecylphenyl)methyl, triphenylmethyl, naphthylmethyl or anthracenylmethyl, preferably benzyl or triphenylmethyl; $C_1$-$C_{20}$ alkyl-substituted or $C_6$-$C_{30}$ aryl-substituted silyl, e.g. methylsilyl, ethylsilyl, phenylsilyl, dimethylsilyl, diethylsilyl, diphenylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyldimethylsilyl, tri-n-pentylsilyl, tri-n-hexylsilyl, tricyclohexylsilyl or triphenylsilyl, preferably trimethylsilyl, tert-butyldimethylsilyl or triphenylsilyl; $C_1$-$C_{20}$ alkoxy, e.g. methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy or n-eicosoxy, preferably methoxy, ethoxy, isopropoxy or tert-butoxy; $C_3$-$C_{20}$ alkylsiloxy, e.g. trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyldimethylsiloxy, tri-n-pentylsiloxy, tri-n-hexylsiloxy or tricyclohexylsiloxy, preferably trimethylsiloxy or tert-butyldimethylsiloxy; $C_1$-$C_{20}$ alkyl-substituted or $C_6$-$C_{30}$ aryl-substituted amino, e.g. dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bistrimethylsilylamino or bis-tert-butyldimethylsilylamino, or corresponding alkyl-substituted phosphine, preferably dimethylamino, diethylamino or diphenylamino; or $C_1$-$C_{20}$ alkyl-substituted or $C_6$-$C_{30}$ aryl-substituted phosphine, e.g. dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, dibenzylphosphine, methylethylphosphine, methylphenylphosphine, benzylhexylphosphine, bistrimethylsilylphosphine or bis-tert-butyldimethylsilylphosphine, preferably dimethylphosphine, diethylphosphine or diphenylphosphine.

X may be: halogen, e.g. fluorine, chlorine, bromine or iodine; $C_1$-$C_{20}$ alkyl other than the Cp derivative, e.g. methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl or n-eicosyl, preferably methyl, ethyl, isopropyl, tert-butyl or amyl; $C_3$-$C_{20}$ cycloalkyl, e.g. cyclopropane, cyclobutyl, cyclopentyl, cyclohexyl, cycloheptyl or adamantyl; $C_6$-$C_{30}$ aryl $C_1$-$C_{20}$ alkyl, e.g. benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-decylphenyl)methyl, (n-tetradecylphenyl)methyl, naphthylmethyl or anthracenylmethyl, preferably benzyl; $C_1$-$C_{20}$ alkoxy, e.g. methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy or n-eicosoxy, preferably methoxy, ethoxy, isopropoxy or tert-butoxy; $C_3$-$C_{20}$ alkylsiloxy, e.g. trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyldimethylsiloxy, tri-n-pentylsiloxy, tri-n-hexylsiloxy or tricyclohexylsiloxy, preferably trimethylsiloxy or tert-butyldimethylsiloxy; $C_1$-$C_{20}$ alkyl-substituted or $C_6$-$C_{30}$ aryl-substituted amino, e.g. dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bistrimethylsilylamino or bis-tert-butyldimethylsilylamino, or corresponding alkyl-substituted phosphine, preferably dimethylamino, diethylamino or diphenylamino; or $C_1$-$C_{20}$ alkyl-substituted or $C_6$-$C_{30}$ aryl-substituted phosphine, e.g. dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, dibenzylphosphine, methylethylphosphine, methylphenylphosphine, benzylhexylphosphine, bistrimethylsilylphosphine or bis-tert-butyldimethylsilylphosphine, preferably dimethylphosphine, diethylphosphine or diphenylphosphine.

The transition metal catalyst represented by Chemical Formula 1 may be used along with a boron compound, an aluminum compound or a mixture thereof as cocatalyst, which can extract the X ligand from the transition metal complex to make the center metal as cation, i.e. to act as counterion, or anion, having a weak binding force. The organoaluminum compound serves to remove trace polar materials, such as water, an catalytic poison, but it may also serve as alkylating agent when the X ligand is halogen.

The boron compound that can be used in the present invention as the cocatalyst may be selected from the group consisting of the compounds represented by the following Chemical Formula 3, Chemical Formula 4 and Chemical Formula 5, which are also disclosed in U.S. Pat. No. 5,198,401:

  [Formula 3]

  [Formula 4]

  [Formula 5]

where B is boron; $R^3$ is phenyl, which may be substituted by 3-5 substituents selected from the group consisting of fluorine, $C_1$-$C_{20}$ alkyl, unsubstituted or substituted by fluorine, and $C_1$-$C_{20}$ alkoxy, unsubstituted or substituted by fluorine; $R^4$ is $C_5$-$C_7$ cycloalkyl radical, $C_1$-$C_{20}$ alkyl $C_6$-$C_{20}$ aryl radical or $C_6$-$C_{30}$ aryl $C_1$-$C_{20}$ alkyl radical, e.g. triphenylmethyl radical; Z is nitrogen or phosphorus; $R^4$ is $C_1$-$C_{20}$ alkyl radical or anilinium radical substituted by two nitrogens and two $C_1$-$C_4$ alkyl groups; and q is an integer 2 or 3.

Preferred examples of the boron-based cocatalyst include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl) borate, tetrakis(2,3,5,6-tetrafluorophenyl) borate, tetrakis(2,3,4,5-tetrafluorophenyl) borate, tetrakis(3,4,5-tetrafluorophenyl) borate, tetrakis(2,2,4-trifluorophenyl) borate, phenylbis(pentafluorophenyl) borate and tetrakis(3,5-bistrifluoromethylphenyl) borate. And, specific examples of the complex thereof include ferrocenium tetrakis(pentafluorophenyl) borate, 1,1'-dimethylferrocenium tetrakis(pentafluorophenyl) borate, silver tetrakis(pentafluorophenyl) borate, triphenylmethyl tetrakis(pentafluorophenyl) borate, triphenylmethyl tetrakis(3,5-bistrifluoromethylphenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(n-butyl)ammonium tetrakis(3,5-bistrifluoromethylphenyl) borate, N,N-dimethylanilinium tetrakis(pentafluorophenyl) borate, N,N-diethylanilinium tetrakis(pentafluorophenyl) borate, N,N-2,4,6-pentamethylanilinium tetrakis (pentafluorophenyl) borate, N,N-dimethylanilinium tetrakis (3,5-bistrifluoromethylphenyl) borate, diisopropylammonium tetrakis(pentafluorophenyl) borate, dicyclohexylammonium tetrakis(pentafluorophenyl) borate, triphenylphosphonium tetrakis(pentafluorophenyl) borate, tri (methylphenyl)phosphonium tetrakis(pentafluorophenyl) and tri(dimethylphenyl)phosphonium borate tetrakis(pentafluorophenyl) borate. The most preferred among them are N,N-dimethylanilinium tetrakispentafluorophenyl borate, triphenylmethylinium tetrakispentafluorophenyl borate or trispentafluoroborane.

The aluminum compound used in the present invention may be an aluminoxane compound represented by the following Chemical Formula 6 or Chemical Formula 7, an organoaluminum compound represented by the following Chemical Formula 8, or an organoaluminum hydrocarbyl oxide compound represented by the following Chemical Formula 9 or Chemical Formula 10:

  [Formula 6]

  [Formula 7]

  [Formula 8]

  [Formula 9]

  [Formula 10]

where $R^7$ is linear or branched $C_1$-$C_{20}$ alkyl, preferably methyl or isobutyl; m and p are integers from 5 to 20; $R^9$ and $R^9$ are $C_1$-$C_{20}$ alkyl; E is hydrogen or halogen; r is an integer from 1 to 3; and $R''$ is $C_1$-$C_{20}$ alkyl or $C_6$-$C_{30}$ aryl.

As specific examples of the aluminum compound, the aluminoxane compound may be methylaluminoxane, modified methylaluminoxane or tetraisobutylaluminoxane; the organoaluminum compound may be a trialkylaluminum, e.g. trimethylaluminum, triethylaluminum, tripropylaluminum, triisobutylaluminum or trihexylaluminum; a dialkylaluminum chloride, e.g. dimethylaluminum chloride, diethylaluminum chloride, dipropylaluminum chloride, diisobutylaluminum chloride or dihexylaluminum chloride; an alkylaluminumdi chloride, e.g. methylaluminumdi chloride, ethylaluminumdi chloride, propylaluminumdi chloride, isobutylaluminumdi chloride or hexylaluminumdi chloride; or a dialkylaluminum hydride, e.g. dimethylaluminum hydride, diethylaluminum hydride, dipropylaluminum hydride, diisobutylaluminum hydride or dihexylaluminum hydride, preferably a trialkylaluminum, more preferably triethylaluminum or triisobutylaluminum, with the molar proportion of center metal M:boron:aluminum being 1:0.1-100:10-1,000, more preferably 1:0.5-5:25-500.

In another aspect, the present invention provides a process for preparing an ethylene homopolymer or a copolymer of ethylene and an α-olefin using the transition metal catalyst system. The process is performed by contacting the transition metal catalyst and the cocatalyst with ethylene monomer or, if necessary, an α-olefin comonomer in the presence of an adequate organic solvent. The transition metal catalyst and the cocatalyst may be added separately into a reactor or may be previously mixed and added into a reactor.

The sequence of addition or mixing condition, including temperature, concentration, etc., is not particularly limited.

Preferably, the organic solvent that may be used in the preparation process is a $C_3$-$C_{20}$ hydrocarbon. Specific examples may include butane, isobutane, pentane, hexane, heptane, octane, isooctane, nonane, decane, dodecane, cyclohexane, methylcyclohexane, benzene, toluene, xylene, and the like.

Specifically, in the preparation of an ethylene homopolymer, ethylene is used as monomer alone. Preferred pressure of ethylene is 1-1,000 atm, more preferably 10-150 atm. And, preferred polymerization temperature is 60-300° C., more preferably 80-250° C.

And, in the preparation of a copolymer of ethylene and an α-olefin, a $C_3$-$C_{18}$ α-olefin may be used as comonomer together with ethylene. Preferably, one selected from the group consisting of propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-octadecene and 1-eicosene may be used. More preferably, 1-butene, 1-hexene, 1-octene or 1-decene may be copolymerized with ethylene. In this case, preferred pressure of ethylene and preferred polymerization temperature are the same as for the preparation of the high density polyethylene. Typically, the ethylene copolymer prepared in accordance with the present invention comprises 50 weight % or more of ethylene, preferably 60 weight % or more, more preferably 60-99 weight % of ethylene. As described earlier, the linear low density polyethylene (LLDPE) prepared using a $C_4$-$C_{10}$ α-olefin as comonomer has a density of 0.910-0.940 g/cc and an olefin copolymer having a density of 0.910-0.860 g/cc can be prepared. Further, in the preparation of an ethylene homopolymer or copolymer in accordance with the present invention, hydrogen may be used for the control of molecular weight. Typically, the homopolymer or copolymer has a weight average molecular weight ($M_w$) of 80,000-500,000.

Since the catalyst composition presented by the present invention exists in homogeneous state in a polymerization reactor, it can be applied to a solution polymerization process which is carried out at a temperature above the melting polymer of the corresponding polymer. It may also be applied to a slurry polymerization or gas phase polymerization process, as disclosed in U.S. Pat. No. 4,752,597, by supporting the transition metal complex and the cocatalyst on a porous metal oxide support.

DESCRIPTION OF DRAWINGS

The above and other features of the present invention will now be described in detail with reference to certain example embodiments thereof illustrated in the accompanying drawing which is given hereinbelow by way of illustration only, and thus is not limitative of the present invention, and wherein:

FIG. 1 shows a crystal structure of dichloro-2-isopropylphenylpentamethylcyclopentadienyltitanium(IV) according to the present invention prepared in Preparation Example 4.

BEST MODE

The following examples further illustrate the present invention, but are not intended to limit the same.

Unless specified otherwise, all the syntheses of ligands and catalysts were carried out under nitrogen atmosphere using standard Schlenk or glove box techniques. The organic solvent used for the reaction was subjected to reflux in the presence of sodium metal and benzophenone to remove water and distilled immediately before use. $^1$H-NMR analysis of the synthesized ligands and catalysts was carried out at room temperature using the Varian Mercury 300 MHz spectrometer.

The polymerization solvent cyclohexane was sequentially passed through columns packed with Q-5 catalyst (BASF), silica gel and activated alumina and subjected to bubbling using high-purity nitrogen prior to use, in order to sufficiently remove water, oxygen or other catalytic poisons. The synthesized polymer was analyzed as follows.

1. Melt Index (MI)

Measured in accordance with ASTM D 2839.

2. Density

Measured in accordance with ASTM D 1505 using a density gradient column.

3. Melting Point ($T_m$)

Measured under nitrogen atmosphere at a rate of 10° C./min under the $2^{nd}$ heating condition using Dupont DSC2910.

4. Molecular Weight and Molecular Weight Distribution

Measured in 1,2,3-trichlorobenzene solvent at 135° C. at a rate of 1.0 mL/min using PL Mixed-BX2+preCol installed PL210 GPC. Molecular weight was corrected using PL polystyrene as standard material.

5. α-Olefin Content (Weight %) in Copolymer

Measured at 120° C. at 125 MHz in $^{13}$C-NMR mode, using the Bruker DRX500 NMR (nuclear magnetic resonance) spectrometer and using a mixture solvent of 1,2,4 trichlorobenzene/$C_6D_6$ (7/3, wt/wt) [Randal, J. C. JMS-Rev. Macromol. Chem. Phys. 1980, C29, 201].

Preparation Example 1

Synthesis of dichloro-2-methylphenoxypentamethylcyclopentadienyltitanium(IV)

2-Methylphenol (0.58 g, 5.05 mmol, Aldrich) was put in a dried flask and dissolved with 40 mL of toluene. After stirring well, the temperature was lowered to 0° C. n-Butyllithium (2.4 mL, 2.5 M in hexane, Aldrich) was slowly added dropwise to the mixture. After keeping the temperature for 1 hour, the temperature was raised to room temperature and stirring was carried out for 12 hours. After removing the solvent layer, the reaction product was washed well with hexane, dried and dissolved again with 40 mL of toluene. The mixture was cooled to 0° C. and pentamethylcyclopentadienyltitanium chloride (1.46 g, 5.05 mmol) dissolved in 10 mL of toluene was slowly added dropwise.

After keeping the temperature for 1 hour, the temperature was raised to room temperature and stirring was carried out for 12 hours. Subsequently, the reaction product was filtered and the volatile components were removed in vacuum. Orange solid was obtained. Thus obtained solid was dissolved in toluene and recrystallized at −15° C. to obtain 1.55 g (yield: 85%) of orange crystal.

$^1$H NMR($C_6D_6$): δ=1.89 (s, 15H, $C_5(CH_3)_5$), 2.20 (s, 3H, $CH_3$), 6.80 (m, 1H, Ph), 6.94 (m, 3H, Ph) ppm.

Preparation Example 2

Synthesis of bis(2-methylphenoxy)pentamethylcyclopentadienyltitanium(IV) chloride 1.16 g (10.14 mmol) of 2-methylphenol (Aldrich, 99%) was dissolved in 40 mL of hexane and 4.8 mL of n-butyllithium (2.5 M hexane solution) was slowly added dropwise at 0° C. White precipitate obtained after 6 hours of reaction at room temperature was separated and washed twice with 10 mL of hexane. After removing the volatile components in vacuum, the product was dissolved again in toluene (10 mL) and 10 mL of trichloropentamethylcyclopentadienyltitanium (IV) (1.64 g, 5.5 mmol) dissolved in toluene was slowly added dropwise at 0° C.

After 1 hour of stirring at room temperature, reflux was carried out for 12 hours. The reaction mixture was filtered and the volatile components were removed. 1.93 g (yield: 81%) of orange solid was obtained after recrystallization at −35° C. from a mixture of toluene/hexane.

$^1$H NMR($C_6D_6$): δ=1.88 (s, 15H, C(CH$_3$)$_5$), 2.21 (s, 6H, CH$_3$), 6.79-6.94 (m, 8H, $C_6H_4$) ppm.

Preparation Example 39

Synthesis of dichloro-2-isopropylphenoxypentamethylcyclopentadienyltitanium(IV)

Preparation Example 1 was repeated except that 2-isopropylphenol (0.72 g, 5.05 mmol, Aldrich) was used instead of 2-phenylphenol and the obtained solid was dissolved in toluene and recrystallized at −15° C. 1.57 g (yield: 800) of orange crystal was obtained.

$^1$H-NMR($C_6D_6$): δ=1.22 (d, 6H, CH(CH$_3$)$_2$, $^3J_{H-H}$=7 Hz), 1.91 (s, 15H, $C_5$(CH$_3$)$_5$), 3.46 (m, 1H, CH(CH$_3$)$_2$), 6.99 (m, 4H, Ph) ppm.

Preparation Example 4

Synthesis of bis(2-isopropylphenoxy)pentamethylcyclopentadienyltitanium(IV) chloride 2.1 g (15.00 mmol) of 2-isopropylphenol (Aldrich, 98%) was dissolved in 40 mL of hexane and 6.0 mL of butyllithium (2.5 M hexane solution) was slowly added dropwise at 0° C.

White precipitate obtained after 6 hours of reaction at room temperature was separated and washed twice with 10 mL of hexane. After removing the volatile components in vacuum, the product was dissolved again in toluene (10 mL), and 10 mL of trichloropentamethylcyclopentadienyltitanium(IV) (2.17 g, 7.5 mmol) dissolved in toluene was slowly added dropwise at 0° C.

After 1 hour of stirring at room temperature, reflux was carried out for 12 hours. The reaction mixture was filtered and the volatile components were removed. 3.04 g (yield: 83%) of orange solid was obtained after recrystallization at −35° C. from a mixture of toluene/hexane.

$^1$H NMR($C_6D_6$): δ=1.21 (d, 14H, CH(CH$_3$)$_2$, $^3J_{H-H}$=7 Hz), 1.91 (s, 15H, C(CH$_3$)$_5$), 3.46 (m, 2H, CH(CH$_3$)$_2$), 6.89-7.09 (m, 8H, $C_6H_4$) ppm.

Preparation Example 5

Synthesis of dichloro-2-tert-butylphenoxypentamethylcyclopentadienyltitanium(IV)

Preparation Example 1 was repeated except that 2-tert-butylphenol (0.79 g, 5.05 mmol, Aldrich) was used instead of 2-phenylphenol. The obtained solid was dissolved in toluene and recrystallized at −15° C. 1.52 g (yield: 75%) of orange crystal was obtained.

$^1$H-NMR($C_6D_6$): δ=1.27 (s, 9H, C(CH$_3$)$_3$, 1.87 (s, 15H, $C_5$(CH$_3$)$_5$), 6.99 (m, 4H, Ph) ppm.

Comparative Preparation Example 1

Synthesis of dichloro-2,6-diisopropylphenoxypentamethylcyclopentadienyltitanium(IV)

Preparation Example 1 was repeated except that 2,6-diisopropylphenol (0.93 g, 5.05 mmol, Aldrich) was used instead of 2-phenylphenol and the obtained solid was dissolved in toluene and recrystallized at −15° C. 1.83 g (yield: 840) of orange crystal was obtained.

$^1$H-NMR($C_6D_6$): δ=1.31 (d, 12H, CH(CH$_3$)$_2$, $^3J_{H-H}$=7 Hz) 1.94 (s, 15H, C(CH$_3$)$_5$), 3.44 (m, 2H, CH(CH$_3$)$_2$), 7.11 (m, 3H, Ph).

Comparative Preparation Example 2

Synthesis of dichloro-2,6-di-tertbutylphenoxypentamethylcyclopentadienyltitanium(IV)

Preparation Example 1 was repeated except that 2,6-di-tert-butylphenol (1.07 g, 5.05 mmol, Aldrich) was used instead of 2-phenylphenol and the obtained solid was dissolved in toluene and recrystallized at −15° C. 1.88 g (yield: 81%) of yellow crystal was obtained.

$^1$H-NMR($C_6D_6$): δ=1.44 (s, 18H, C(CH$_3$)$_3$), 1.82 (s, 15H, C(CH$_3$)$_5$), 6.82 (t, 1H, Ph, $^3J_{H-H}$=7 Hz), 7.16 (d, Ph, $^3J_{H-H}$=7 Hz).

Comparative Preparation Example 3

Synthesis of dichloro-2,6-diphenylphenoxypentamethylcyclopentadienyltitanium(IV)

Preparation Example 1 was repeated except that 2,6-diphenylphenol (1.27 g, 5.05 mmol, Aldrich) was used instead of 2-phenylphenol and the obtained solid was dissolved in toluene and recrystallized at −15° C. 1.97 g (yield: 78%) of yellow crystal was obtained.

$^1$H-NMR($C_6D_6$): δ=1.46 (s, 15H, C(CH$_3$)$_3$), 6.92 (t, 3H, Ph, $^3J_{H-H}$=7 Hz), 7.16 (m, 4H, Ph), 7.33 (t, 4H, Ph, $^3J_{H-H}$=7 Hz), 7.64 (d, 4H, Ph, $^3J_{H-H}$=7 Hz).

Example 1

100 mL of cyclohexane was put in a 200 mL stainless steel reactor sufficiently dried and purged with nitrogen.

Subsequently, 3 mL of mMAO-7 (Akzo-Nobel) 45 mM toluene solution was added. After heating the reactor to 140° C., ethylene was filled in the reactor. 0.5 mL of dichloro-2-methylphenoxypentamethylcyclopentadienyltitanium(IV) (1.0 mM toluene solution) synthesized in Preparation Example 1 and 0.3 mL of 5 mM triphenylmethyliniumtetrakispentafluorophenyl borate (99%, Boulder Scientific) toluene solution were sequentially added to initiate polymerization. The ethylene pressure was maintained at 30 atm. Within 2 minutes of reaction, the temperature of the reactor reached 181° C. 10 minutes after the commencing of the reaction, 10 mL of ethanol (10 vol % HCl solution) was added to terminate the polymerization. After stirring for 4 hours using 1,500 mL of ethanol, the reaction product was filtered and separated. The collected reaction product was dried in a vacuum oven at 60° C. for 8 hours. 4.3 g of polymer was obtained. The polymer had a melting point of 139.3° C., a melt index of not more than 0.001 g/10 min, a weight average molecular weight of 224,600 and a molecular weight distribution of 2.95 (gel chromatography).

Example 2

Polymerization was carried out in the same manner as in Example 1, except for using 1.0 mL of dichloro-2-methylphenoxypentamethylcyclopentadienyltitanium(IV) (1.0 mM toluene solution) synthesized in Preparation Example 1. Within 2 minutes of polymerization, the temperature of the reactor reached 177° C. 6.4 g of dried polymer was obtained. The polymer had a melting point of 118.7° C., a melt index of 1.7 g/10 min, a weight average molecular weight of 139,000 and a molecular weight distribution of 2.5 (gel chromatography).

Further, it had a density of 0.9052 and a 1-octene content of 14.4 weight %.

Example 3

Polymerization was carried out in the same manner as in Example 1, except for using 1.0 mL of bis(2-methylphenoxy)pentamethylcyclopentadienyltitanium(IV) chloride (1.0 mM toluene solution) synthesized in Preparation Example 2 and 0.5 mL of 5 mM triphenylmethyliniumtetrakispentafluorophenyl borate (99%, Boulder Scientific) toluene solution. Within 2 minutes of polymerization, the temperature of the reactor reached 182° C.

5.3 g of dried polymer was obtained. The polymer had a melting point of 139.3° C., a melt index of not more than 0.001 g/10 min, a weight average molecular weight of 272,000 and a molecular weight distribution of 2.18 (gel chromatography).

Example 4

Polymerization was carried out in the same manner as in Example 1, except for using 0.5 mL of dichloro-2-isopropylphenoxypentamethylcyclopentadienyltitanium(IV) (1.0 mM toluene solution) synthesized in Preparation Example 3.

Within 2 minutes of polymerization, the temperature of the reactor reached 173° C. 5.1 g of dried polymer was obtained.

The polymer had a melting point of 138.6° C., a melt index of not more than 0.001 g/10 min, a weight average molecular weight of 460,300 and a molecular weight distribution of 4.4 (gel chromatography).

Example 5

Polymerization was carried out in the same manner as in Example 2, except for using 1.0 mL of dichloro-2-isopropylphenoxypentamethylcyclopentadienyltitanium(IV) (1.0 mM toluene solution) synthesized in Preparation Example 3.

Within 2 minutes of polymerization, the temperature of the reactor reached 184° C. 5.2 g of dried polymer was obtained.

The polymer had a melting point of 118.7° C., a melt index of 3.7 g/10 min, a weight average molecular weight of 139,000 and a molecular weight distribution of 2.5 (gel chromatography).

Further, it had a density of 0.9022 and a 1-octene content of 15.9 weight %.

Example 6

Polymerization was carried out in the same manner as in Example 1, except for using 4 mL of mMAO-7 (Akzo-Nobel) 45 mM toluene solution, 1.0 mL of bis(2-isopropylphenoxy)pentamethylcyclopentadienyltitanium(IV) chloride (1.0 mM toluene solution) synthesized in Preparation Example 4 and 0.5 mL of 5 mM triphenylmethyliniumtetrakispentafluorophenyl borate (99%, Boulder Scientific) toluene solution. Within 2 minutes of polymerization, the temperature of the reactor reached 179° C.

5.6 g of dried polymer was obtained. The polymer had a melting point of 137.7° C., a melt index of not more than 0.001 g/10 min, a weight average molecular weight of 240,300 and a molecular weight distribution of 2.13 (gel chromatography).

Example 7

Polymerization was carried out in the same manner as in Example 2, except for using 1.0 mL of bis(2-isopropylphenoxy)pentamethylcyclopentadienyltitanium(IV) chloride (1.0 mM toluene solution) synthesized in Preparation Example 4. Within 2 minutes of polymerization, the temperature of the reactor reached 174° C. 5.0 g of dried polymer was obtained. The polymer had a melting point of 118.7° C., a melt index of 1.2 g/10 min, a weight average molecular weight of 139,000 and a molecular weight distribution of 2.5 (gel chromatography). Further, it had a density of 0.9024 and a 1-octene content of 15.8 weight %.

Example 8

Polymerization was carried out in the same manner as in Example 1, except for using 1.0 mL of dichloro-2-tert-butylphenoxypentamethylcyclopentadienyltitanium(IV) (1.0 mM toluene solution) synthesized in Preparation Example 5. Within 2 minutes of polymerization, the temperature of the reactor reached 186° C. 5.7 g of dried polymer was obtained. The polymer had a melting point of 138.6° C., a melt index of not more than 0.001 g/10 min, a weight average molecular weight of 289,300 and a molecular weight distribution of 2.3 (gel chromatography).

Example 9

Polymerization was carried out in the same manner as in Example 2, except for using 1.0 mL of dichloro-2-isopropylphenoxypentamethylcyclopentadienyltitanium(IV) (1.0 mM toluene solution) synthesized in Preparation Example 5.

Within 2 minutes of polymerization, the temperature of the reactor reached 178° C. 4.9 g of dried polymer was obtained.

The polymer had a melting point of 118.7° C., a melt index of 2.4 g/10 min, a weight average molecular weight of 139,000 and a molecular weight distribution of 2.5 (gel chromatography). Further, it had a density of 0.9074 and a 1-octene content of 13.3 weight %.

Comparative Example 1

Polymerization was carried out in the same manner as in Example 8, except for using 1.0 mL of dichloro-2,6-diisopropylphenoxypentamethylcyclopentadienyltitanium(IV) (1.0 mM toluene solution) synthesized in Comparative Preparation Example 1. Within 2 minutes of polymerization, the temperature of the reactor reached 162° C. 3.9 g of dried polymer was obtained. The polymer had a melting point of 138.9° C., a melt index of not more than 0.001 g/10 min, a weight average molecular weight of 264,300 and a molecular weight distribution of 2.8 (gel chromatography).

Comparative Example 2

Polymerization was carried out in the same manner as in Example 2, except for using 1.0 mL of dichloro-2,6-diisopropylphenoxypentamethylcyclopentadienyltitanium(IV) (1.0 mM toluene solution) synthesized in Comparative Preparation Example 1. Within 2 minutes of polymerization, the temperature of the reactor reached 163° C. 3.5 g of dried polymer was obtained. The polymer had a melting point of 118.7° C., a melt index of 1.3 g/10 min, a weight average molecular weight of 139,000 and a molecular weight distribution of 2.5 (gel chromatography). Further, it had a density of 0.9061 and a 1-octene content of 13.9 weight.

Comparative Example 3

Polymerization was carried out in the same manner as in Example 8, except for using 1.0 mL of dichloro-2,6-di-tert-butylphenoxypentamethylcyclopentadienyltitanium(IV) (1.0 mM toluene solution) synthesized in Comparative Preparation Example 2. Within 2 minutes of polymerization, the temperature of the reactor reached 161° C. 3.0 g of dried polymer was obtained. The polymer had a melting point of 138.9° C., a melt index of not more than 0.001 g/10 min, a weight average molecular weight of 252,300 and a molecular weight distribution of 2.9 (gel chromatography).

Comparative Example 4

Polymerization was carried out in the same manner as in Example 2, except for using 1.0 mL of dichloro-2,6-di-tert-butylphenoxypentamethylcyclopentadienyltitanium(IV) (1.0 mM toluene solution) synthesized in Comparative Preparation Example 2. Within 2 minutes of polymerization, the temperature of the reactor reached 161° C. 3.0 g of dried polymer was obtained. The polymer had a melting point of 118.7° C., a melt index of 0.5 g/10 min, a weight average molecular weight of 139,000 and a molecular weight distribution of 2.5 (gel chromatography). Further, it had a density of 0.9115 and a 1-octene content of 11.0 weight.

Comparative Example 5

Polymerization was carried out in the same manner as in Example 8, except for using 1.0 mL of dichloro-2,6-diphenylphenoxypentamethylcyclopentadienyltitanium(IV) (1.0 mM toluene solution) synthesized in Comparative Preparation Example 3. Within 2 minutes of polymerization, the temperature of the reactor reached 161° C. 4.0 g of dried polymer was obtained. The polymer had a melting point of 137.9° C., a melt index of not more than 0.001 g/10 min, a weight average molecular weight of 360,900 and a molecular weight distribution of 2.5 (gel chromatography).

Comparative Example 6

Polymerization was carried out in the same manner as in Example 2, except for using 1.0 mL of dichloro-2,6-diphenylphenoxypentamethylcyclopentadienyltitanium(IV) (1.0 mM toluene solution) synthesized in Comparative Preparation Example 3. Within 2 minutes of polymerization, the temperature of the reactor reached 160° C. 2.9 g of dried polymer was obtained. The polymer had a melting point of 118.7° C., a melt index of 0.21 g/10 min, a weight average molecular weight of 139,000 and a molecular weight distribution of 2.5 (gel chromatography). Further, it had a density of 0.9138 and a 1-octene content of 10.1 weight %.

TABLE 1

| | Catalyst | Amount of catalyst (µmol) | Polymerization temperature, initial (° C.) | Highest polymerization temperature (° C.) | Polymer (g) | $M_w$ (g/mol) | $M_w/M_n$ |
|---|---|---|---|---|---|---|---|
| Ex. 1 | Prep. Ex. 1 | 0.5 | 140 | 173 | 4.3 | 224,000 | 2.95 |
| Ex. 3 | Prep. Ex. 2 | 1.0 | 140 | 182 | 5.3 | 272,000 | 2.18 |
| Ex. 4 | Prep. Ex. 3 | 0.5 | 140 | 173 | 5.1 | 460,000 | 4.40 |
| Ex. 6 | Prep. Ex. 4 | 1.0 | 140 | 179 | 5.6 | 240,000 | 2.13 |
| Ex. 8 | Prep. Ex. 5 | 1.0 | 140 | 186 | 5.7 | 289,000 | 2.30 |
| Comp. Ex. 1 | Comp. Prep. Ex. 1 | 1.0 | 140 | 162 | 3.9 | 264,000 | 2.8 |
| Comp. Ex. 3 | Comp. Prep. Ex. 2 | 1.0 | 140 | 161 | 3.0 | 252,000 | 2.9 |
| Comp. Ex. 5 | Comp. Prep. Ex. 3 | 1.0 | 140 | 163 | 4.0 | 260,000 | 2.5 |

TABLE 2

| | Catalyst | Amount of catalyst (mol) | Injection amount of 1-octene (mL) | Polymerization temperature, initial (° C.) | Highest polymerization temperature (° C.) | Polymer (g) | MI (g/10 min) | Octene content (wt %) |
|---|---|---|---|---|---|---|---|---|
| Ex. 2 | Prep. Ex. 1 | 1.0 | 8 | 140 | 177 | 6.4 | 1.7 | 14.4 |

TABLE 2-continued

| | Catalyst | Amount of catalyst (mol) | Injection amount of 1-octene (mL) | Polymerization temperature, initial (° C.) | Highest polymerization temperature (° C.) | Polymer (g) | MI (g/10 min) | Octene content (wt %) |
|---|---|---|---|---|---|---|---|---|
| Ex. 5 | Prep. Ex. 3 | 1.0 | 8 | 140 | 184 | 5.2 | 3.7 | 15.9 |
| Ex. 7 | Prep. Ex. 4 | 1.0 | 8 | 140 | 174 | 5.0 | 1.2 | 15.8 |
| Ex. 9 | Prep. Ex. 5 | 1.0 | 8 | 140 | 178 | 4.9 | 2.4 | 13.3 |
| Comp. Ex. 2 | Comp. Prep. Ex. 1 | 1.0 | 8 | 140 | 163 | 3.5 | 1.3 | 13.9 |
| Comp. Ex. 4 | Comp. Prep. Ex. 2 | 1.0 | 8 | 140 | 161 | 3.0 | 0.5 | 11.0 |
| Comp. Ex. 6 | Comp. Prep. Ex. 3 | 1.0 | 8 | 140 | 160 | 2.9 | 0.2 | 10.1 |

As can be seen from Tables 1 and 2, homopolymerization of ethylene and copolymerization of ethylene and 1-octene were more efficient in polymer yield in Examples 1-9 under high temperature polymerization condition of 140° C. than Comparative Examples 1-6. Further, olefin copolymers having higher 1-octene content were prepared under the same condition.

The present invention has been described in detail with reference to example embodiments thereof. However, it will be appreciated by those skilled in the art that change may be made in these embodiments without departing from the principles and spirit of the invention, the scope of which is defined in the accompanying claims and their equivalents.

INDUSTRIAL APPLICABILITY

The transition metal complex according to the present invention and the catalyst composition comprising the same can be synthesized in high yield using easily manageable and environment-friendly raw materials. Further, they may be used in a solution polymerization carried out at a high temperature to provide high molecular weight olefin polymers with high catalytic activity. Further, they are useful in the preparation of higher grade α-olefin copolymers.

Accordingly, they are more practical than previously known non-metallocene based single-site catalysts and are useful in the preparation of ethylene homopolymers or copolymers of ethylene and α-olefins having various physical properties.

The invention claimed is:

1. A transition metal catalyst composition for the preparation of an ethylene homopolymer or a copolymer of ethylene and an α-olefin comprising:
    a transition metal complex represented by the following Chemical Formula 1; and
    an alkylaluminoxane or organoaluminum cocatalyst, a boron compound cocatalyst or a mixture thereof:

[Formula 1]

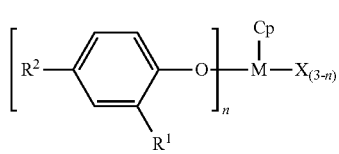

wherein
M is a group IV transition metal;
Cp is capable of forming a $\eta^5$-bonding with M, and is a cyclopentadienyl ring unsubstituted or substituted by $C_1$-$C_{20}$ alkyl, $C_6$-$C_{30}$ aryl, $C_2$-$C_{20}$ alkenyl or $C_6$-$C_{30}$ aryl $C_1$-$C_{20}$ alkyl, or a fused ring unsubstituted or substituted by $C_1$-$C_{20}$ alkyl, $C_6$-$C_{30}$ aryl, $C_2$-$C_{20}$ alkenyl or $C_6$-$C_{30}$ aryl $C_1$-$C_{20}$ alkyl having a cyclopentadienyl ring;
$R^1$ is $C_1$-$C_{20}$ alkyl or $C_6$-$C_{30}$ aryl or $C_1$-$C_{10}$ alkyl;
$R^2$ is hydrogen, halogen, linear or branched $C_1$-$C_{20}$ alkyl optionally substituted by one or more halogen, linear or branched $C_1$-$C_{20}$ alkyl-substituted silyl optionally substituted by one or more halogen, $C_6$-$C_{30}$ aryl optionally substituted by one or more halogen, $C_6$-$C_{30}$ aryl $C_1$-$C_{10}$ alkyl optionally substituted by one or more halogen, $C_1$-$C_{20}$ alkoxy optionally substituted by one or more halogen, $C_3$-$C_{20}$ alkyl-substituted or $C_6$-$C_{20}$ aryl substituted siloxy, $C_1$-$C_{20}$ alkyl-substituted or $C_6$-$C_{30}$ aryl-substituted amino, $C_1$-$C_{20}$ alkyl-substituted or $C_6$-$C_{30}$ aryl-substituted phosphine, $C_1$-$C_{20}$ alkyl-substituted mercapto, or nitro;
n is an integer 1 or 2; and
X is independently halogen, $C_1$-$C_{20}$ alkyl, $C_3$-$C_{20}$ cycloalkyl, $C_6$-$C_{30}$ aryl $C_1$-$C_{20}$ alkyl, $C_1$-$C_{20}$ alkoxy, $C_3$-$C_{20}$ alkylsiloxy, $C_1$-$C_{20}$ alkyl-substituted or $C_6$-$C_{30}$ aryl-substituted amino, $C_1$-$C_{20}$ alkyl-substituted or $C_6$-$C_{30}$ aryl-substituted phosphine, or $C_1$-$C_{20}$ alkyl-substituted mercapto.

2. The transition metal catalyst composition for the preparation of an ethylene homopolymer or a copolymer of ethylene and an α-olefin according to claim 1, wherein the alkylaluminoxane or organoaluminum cocatalyst is selected from the group consisting of methylaluminoxane, modified methylaluminoxane, tetraisobutylaluminoxane, trialkylaluminum, trimethylaluminum, triisobutylaluminum and a mixture thereof.

3. The transition metal catalyst composition for the preparation of an ethylene homopolymer or a copolymer of ethylene and an α-olefin according to claim 1, wherein the proportion of the transition metal to the cocatalyst is 1:50 to 1:5,000, based on the molar ratio of transition metal (M):aluminum.

4. The transition metal catalyst composition for the preparation of an ethylene homopolymer or a copolymer of ethylene and an α-olefin according to claim 1, wherein the boron compound cocatalyst is selected from the group consisting of N,N-dimethylanilinium tetrakispentafluorophenyl borate and triphenylmethylinium tetrakispentafluorophenyl borate.

5. The transition metal catalyst composition for the preparation of an ethylene homopolymer or a copolymer of ethylene and an α-olefin according to claim 1, wherein the proportion of the transition metal to the cocatalyst is 1:0.5-5:25-500 based on the molar ratio of transition metal (M):boron:aluminum.

6. A process for preparing an ethylene homopolymer or a copolymer of ethylene and an α-olefin using the transition metal catalyst composition according to claim 1, wherein a comonomer polymerized with the ethylene is at least one selected from the group consisting of propylene, 1-butene, 1-pentene, 1-hexene, 1-heptene, 1-octene, 1-decene, 1-undecene, 1-dodecene, 1-tetradecene, 1-hexadecene and 1-eicosene, and the ethylene content in the copolymer of ethylene and an α-olefin is at least 60 weight %.

7. The process for preparing an ethylene homopolymer or a copolymer of ethylene and an α-olefin according to claim 6, wherein a polymerization is carried out in a polymerization system at a pressure of 6-150 atm and at a polymerization temperature of 80-250° C.

* * * * *